United States Patent [19]

Hinshaw et al.

[11] 4,281,547
[45] Aug. 4, 1981

[54] ELECTRONIC MINE ROOF BOLT TESTER

[75] Inventors: Stanley E. Hinshaw; Charles F. Cole, Jr., both of Ponca City, Okla.

[73] Assignee: Conoco, Inc. (formerly Continental Oil Company), Ponca City, Okla.

[21] Appl. No.: 37,691

[22] Filed: May 10, 1979

[51] Int. Cl.³ ............................................. G01N 29/04
[52] U.S. Cl. ......................................... 73/579; 73/582
[58] Field of Search ................. 73/579, 582, 584, 588, 73/589, 594, 586, 611, 614

[56] References Cited

U.S. PATENT DOCUMENTS

| 2,635,746 | 4/1953 | Gordon | 73/579 X |
| 3,531,983 | 10/1970 | Heath et al. | 73/584 |
| 3,550,434 | 12/1970 | Schroeder et al. | 73/579 |
| 4,062,229 | 12/1977 | Godfrey et al. | 73/582 |
| 4,128,011 | 12/1978 | Savage et al. | 73/579 |

FOREIGN PATENT DOCUMENTS 557318  6/1977  U.S.S.R. ................................. 73/579

Primary Examiner—James J. Gilu
Attorney, Agent, or Firm—William J. Miller

[57] ABSTRACT

The integrity of mine roofs and rock bolts is tested by determining the natural frequencies of the roof and bolt. The roof is struck at a plurality of locations and the resulting vibrations sensed with accelerometers. The output of each accelerometer is separated into a plurality of signals of different frequencies by a comb filter having selected band passes. The amplitude of the outputs of each of the band passes of the filter are used to determine the condition of the roof and bolt adjacent each accelerometer. The high amplitude signal resulting from the initial impact of the striking implement is electrically gated from the accelerometer output.

9 Claims, 3 Drawing Figures

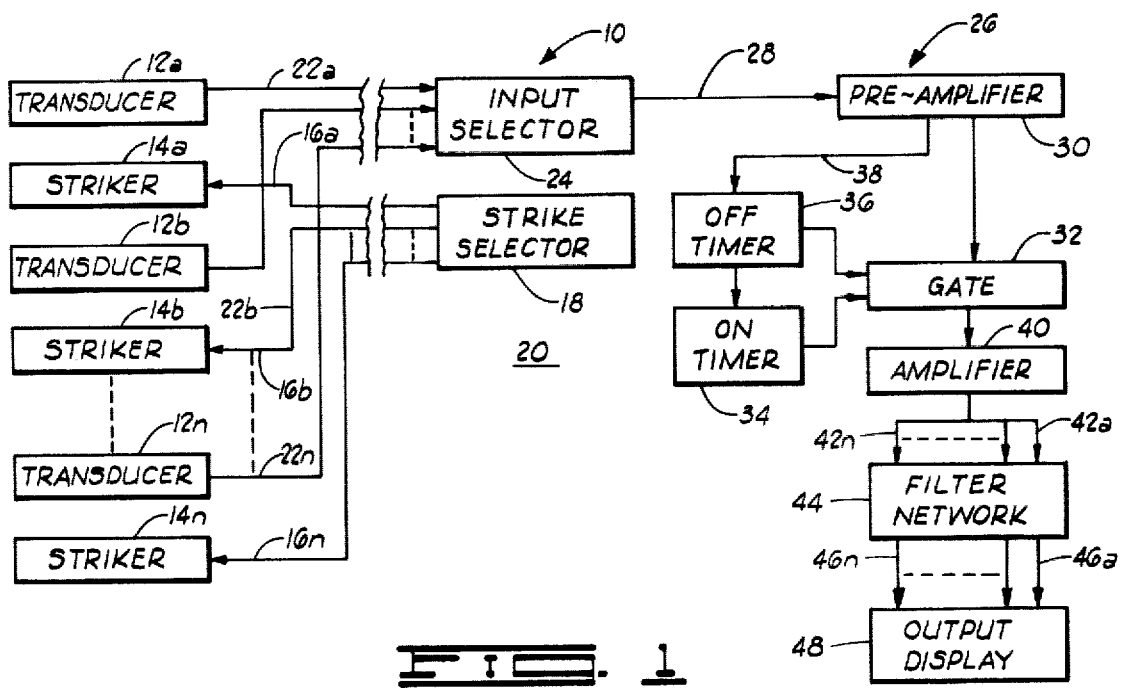
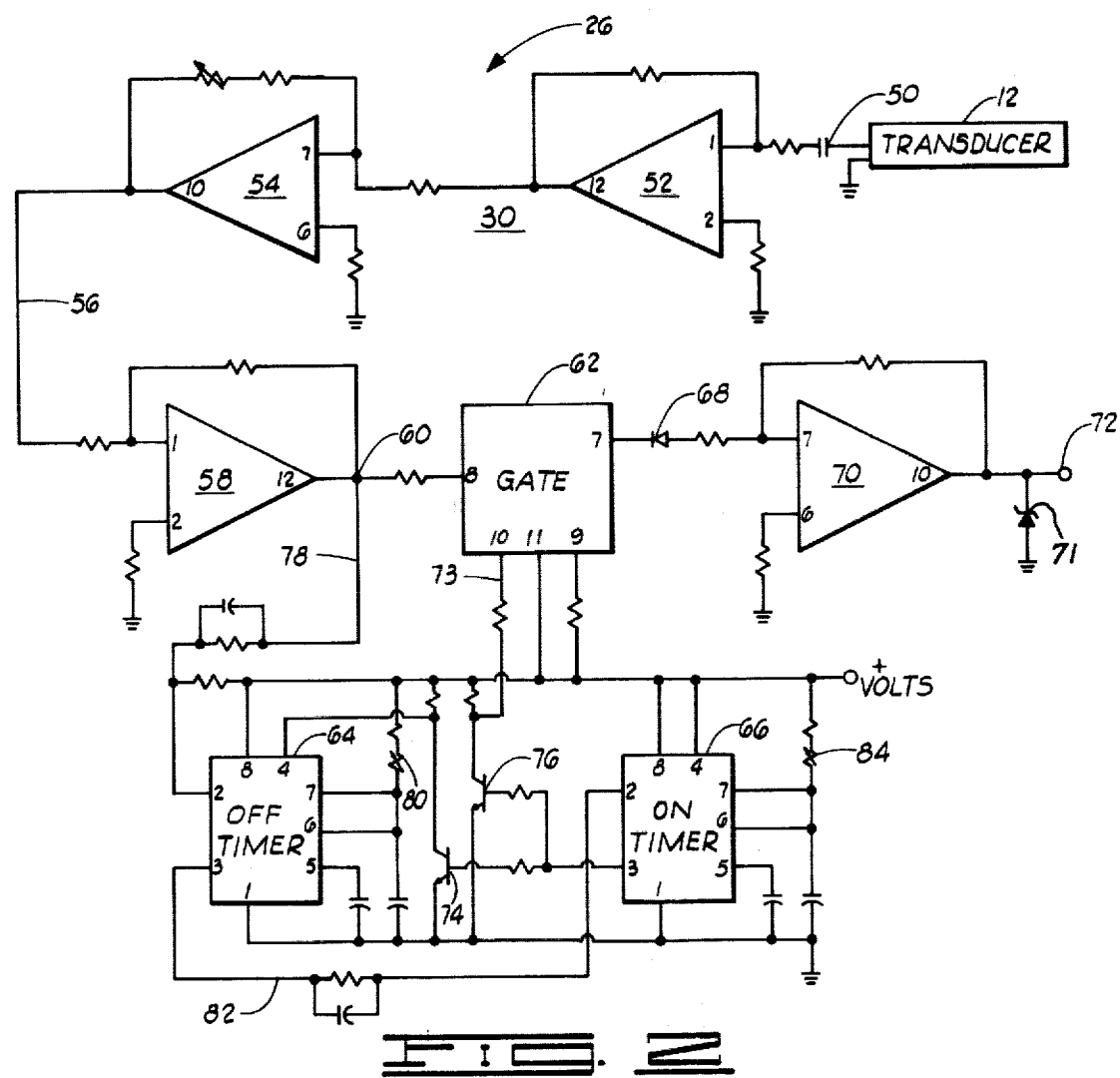

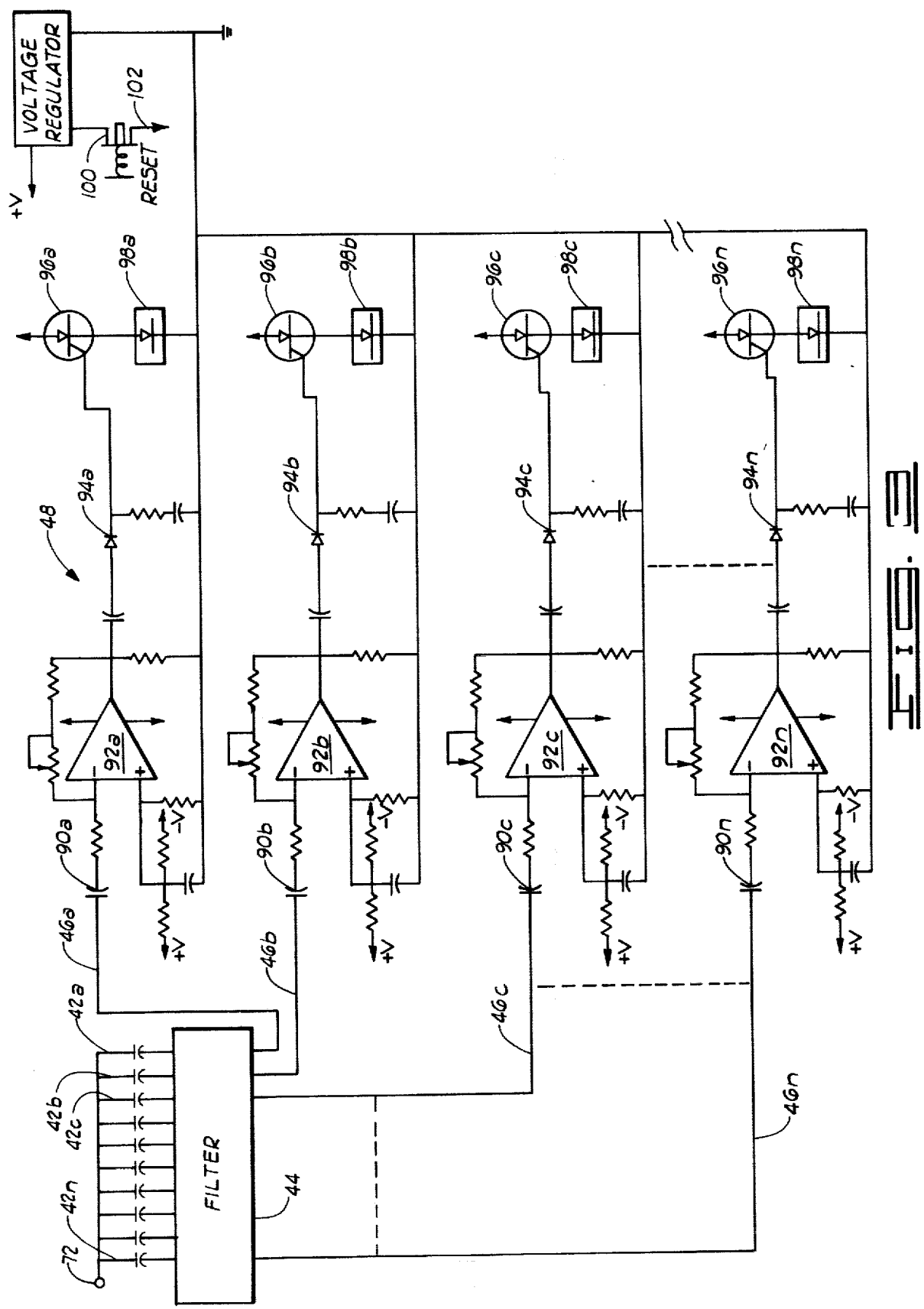

ELECTRONIC MINE ROOF BOLT TESTER

BACKGROUND OF THE INVENTION

1. Field of the Invention

The invention relates to mine safety and surveillance apparatus for determining the stability of mine roof structures and, more particularly, but not by way of limitation, it relates to apparatus for use in determining mine roof bolt tension.

Cross-Reference to Related Application

The present application is related to a co-pending application entitled "Method of Determining Mine Roof Stability", Ser. No. 969,079 as filed on Dec. 13, 1978 and assigned to the present assignee.

2. Description of the Prior Art

The prior art would include the basic method of testing the integrity of installed rock bolts as is set forth in U.S. Pat. No. 4,062,229 wherein grouted roof bolts are excited by a hammer or the like and vibrations are analyzed by a narrow band spectrum analyzer for subsequent plotting in terms of amplitude versus frequency to provide indication of the rock bolt integrity. Other prior art of note will be U.S. Pat. No. 3,290,922 which functions to determine the amount of vacuum in a fruit jar by transmitting a sonic wave into the lid of the fruit jar and detecting a return frequency for indication of deformation of the fruit jar lid, such deformation being caused by the vacuum inside the jar. Microphone pickup is used as the receiver and the output is passed through a wide band amplifier for subsequent frequency discrimination in each of a plurality of successive 100 cycle frequency bands to provide indication. There appears to be no other apparatus of sufficient similarity to the present invention which consists of a specialized circuit approach to provision of mine roof stability testing procedures.

SUMMARY OF THE INVENTION

The present invention contemplates an electronic apparatus for determining the natural mechanical vibrating frequency of a mine roof bolt or associated roof structure. Mechanically excited roof structure is sensed to pick up vibrations emanating therefrom for subsequent amplification and processing through a 200–400 Hz comb filter structure having 10 selected band passes within the limits. The output from each of the individual band pass channels is then applied to a visual indicator that provides indication of the presence of signals in the particular frequency band.

Therefore, it is an object of the present invention to provide an economical and reliable system for testing of mine roof structures as required.

It is also an object of the present invention to provide compact, electronic apparatus for testing and providing direct readout of mine roof stability, rock bolt tension and the like.

Finally, it is an object of the present invention to provide roof bolt testing apparatus which is more readily adaptable for automation and mine system installation.

Other objects and advantages of the invention will be evident from the following detailed description when read in conjunction with the accompanying drawings which illustrate the invention.

BRIEF DESCRIPTION OF THE DRAWING

FIG. 1 is a block diagram of the present invention when installed as a wide area mine safety system;

FIG. 2 is a schematic diagram of amplifier timing circuitry of the present invention; and FIG. 3 is a schematic diagram of indicator circuitry as constructed in accordance with the present invention.

DETAILED DESCRIPTION OF THE INVENTION

FIG. 1 illustrates a system 10 as it may be installed on a relatively permanent basis to monitor particularly hazardous or critical mine locations with interrogation and data analysis carried out at a central or remote location. Thus, a plurality of transducers 12a–n may be positioned at designated locations for detection of energy in either a roof bolt or a roof surface position. A plurality of strikers 14a–n are then similarly located in proximate relationship to the related transducer 2a–n. Strikers 14 may be such as solenoid-type strikers as electrically actuated via lines 16a–n from a strike selector 8 located at the remote operating position 20. Signals detected by transducers 12a–n are then returned via lines 22a–n to a remote input selector 24 which then applies the signals in designated order or selection to test apparatus 26, to be more fully described below.

Selected input from input selector 24 is applied via line 28 to a preamplifier 30 with output applied to a gate circuit 32. Gate 32 is opened and closed by ON timer 34 and OFF timer 36 as controlled by an initiation signal on lead 38 from preamplifier 30. The apparatus 26 is presently constructed of IC circuitry and the preamplifier 30 may be such as a Type 747 operational amplifier, one or more stages, and the gate 32 may be an analog type NAND gate such as Fairchild Type AH0134CD. The timer circuits 34 and 36 may each consist of a bi-stable timer circuit such as Signetics Type NE555.

Output from gate 32 is then applied to an amplifier circuit 40 which provides a plurality of parallel outputs 42a–n to a comb filter network 44 that provides a plurality of frequency selective throughputs with output on respective leads 46a–n. In present construction, the filter network 44 is a conventional type covering the range of frequencies from 200 Hz. to 400 Hz. and it provides ten consecutive throughput channels each 20 Hz. wide. Thus, output signal on leads 46a–n may each carry a signal from one of the ten 20 Hz. band filters, and if this signal is present it will energize a respective associated indication at output display 48. Output display 48 may be such as ten separate LED channels which are selectively energized in accordance with comb filter inputs.

The operator can test selected locations by means of strike selector 18 working in conjunction with input selector 24, and as signal is received and input to preamplifier 30 the LED output display 48 will indicate the signal response characteristics by illumination of selected ones of 10 LED's, each representing a particular 20 Hz. segment between 200 and 400 Hz. The 200–400 Hz. range is selected as being a good indicator range for both roof bolt and roof stability indications as can be seen from FIGS. 2 and 3. However, it should be understood that this range and number of segments is entirely a matter of choice and can be altered in accordance with the exigencies of particular situations.

FIGS. 2 and 3 illustrate the test apparatus 26 in greater detail. With reference particularly to FIG. 2, naturally occurring roof vibration is picked up by a transducer 12, e.g. a well-known type of accelerometer, and applied to a two-stage pre-amplifier 30 whereupon the signal is preprocessed and conducted for further frequency processing. Transducer input is applied through a coupling capacitor 50 to the input of an operational amplifier 52 (type 747 op-amp). Amplified output is then applied in the usual manner to the input of a succeeding stage operational amplifier 54 with output conduction via line 56 which is then applied as input to a first amplifier 58 (type 747 op-amp).

Signal output present at amplifier output junction 60 is then applied through an analog gate 62 under control of a bi-stable OFF timer 64 and bi-stable ON timer 66 to provide gated output via limiter diode 68 for input to a second amplifier 70. Output from amplifier 70 is then applied to a zener diode 71, a threshold limitor, and available at junction point 72 for application to the filter and display circuitry of FIG. 3, as will be described. The gate 62 is enabled by control input on lead 73 and switching transistors 74 and 76. The initial presence of amplified signal at junction 60 is conducted by a lead 78 for input at the No. 2 pin of OFF timer 64 to trigger ON timer 64 thereby assuring that gate 62 is closed for a pre-set time, e.g., 130 milliseconds. This initial gate blocking is utilized to delete the initial striking noise and unwanted transients coming from transducer 12. Off timer 64 is controlled as to operative duration by means of a potentiometer 80 and, when triggered on, the OFF timer 64 provides an output via lead 82 for input actuation at pin No. 2 of ON timer 66. The ON timer 66 has actuation duration controlled by means of a potentiometer 84 and is adjusted so that output from control transistor 76 and control input 73 maintain gate 62 open for a duration sufficient that all of the naturally occurring mechanical vibrations pass through for amplification at final output stage 70.

Thus, given a selected duration of signal, e.g., 1 second as set by potentiometer 84, the electrical signal representative of the naturally occuring roof vibrations is amplified and presented at junction 72 for presentation to the filter network 44 and output display 48. See FIG. 3. The signal input at junction 72 is then applied through ten parallel input paths 42a-42n to a 10-channel comb filter 44 which processes the signal in ten consecutive band pass segments. That is, the channel 42a will output signal within the 200-220 Hertz range, channel b outputs signal in the 220-240 Hertz range, channel c outputs signal in the 240-260 Hertz range, and so forth throughout the full 200 Hz to 400 Hz frequency band, the final or tenth channel outputting signal in the 380-400 Hz. range. It should also be understood that while a 10-channel filter is selected for illustration, there may be any number of frequency channels and allotments utilized depending upon the exigencies of the particular application.

Band pass outputs from filter 44 are then applied via individual conductors 46a-46n to respective amplifier and display devices within output display 48. Thus, the lead 46a is applied through a coupling capacitor 90a for input to an amplifier 92a, e.g., an operational amplifier that may be one-quarter section of a type RN 3641D integrated circuit. Output from amplifier 92a is then rectified by a diode 94a and, if present, rectified positive voltage is applied to the gate electrode of a semiconductive control LED rectifier 96a, e.g., type 2N5062. When the SCR 96a is rendered conductive, the light emitting diode 98a is caused to illuminate thereby to indicate frequency presence within the first frequency range of comb filter 44, presence within the first frequency range of comb filter 44, i.e., the 200-220 Hz range. Presence of sufficient signal energy in any of the other allotted frequency bands as present on input leads 46b-n will similarly provide amplified signal through respective amplifiers 92b-n and diodes 94b-n to illuminate their respective light emitting diodes 98b-n. Thus, the display output of the ten (or more in such cases) light emitting diodes 98a -n will provide indications of signal within their respective frequency allotments within the 200-400 Hz range so that the operator can rapidly derive an indication as to mine roof stability for the tested mine locale.

The actual method of reading roof bolt or mine roof stability is fully disclosed in the aforementioned co-pending application, Ser. No. 969,079 entitled "Method of Determining Mine Roof Stability" as filed Dec. 13, 1978. Sampling of the natural response frequency bands in the range of 0 to 1000 Hertz will provide indications as to roof and bolt stability. Presence of high amplitude modal frequency responses in the lower half of the range indicate lesser roof bolt tension, and a shift in, for example, the third or fourth harmonic mode toward a higher frequency will indicate increasing roof bolt tension.

In like manner, overall roof stability may be indicated by examining frequency response in the same range. Strong, predominant response in the 0 to 400 Hertz range will indicate a weak roof response, while absence of response at 0 to 400 Hertz indicates a strong roof response, the natural occuring frequencies actually occurring above 500 Hertz.

After a selected test has been run, a reset push button switch 100 can be actuated to provide reset voltage output on a lead 102 which leads to each of the respective SCR elements 96a-96n to quench the SCR conduction and respective LED indications until a next successive test is run. Thus, the test unit is in readiness for operation of a selected striker with pickup of energy by the respectively located transducer for input via a preamplifier 30 to the gating and display circuitry as shown in FIGS. 2 and 3. In addition to direct visual output display, it is contemplated that derived frequency indications will be recorded and input to an associated digital computer equipment whereby detailed mine roof stability data can be stored with continual update and readout availability.

The foregoing discloses a novel mine roof stability testing device which functions to test by analyzing the frequency content of naturally occurring radiation of mine roof bolts and mine roof earth structure. The device of the present invention provides accurate and reliable readout in a most economical manner as the equipment is of relatively low cost yet highly reliable nature. In addition, the character of the data readout is fully compatible with various digital computer techniques and programs such that continual and complete mine surveillance can be carried out for designated areas.

Changes may be made in the combination and arrangement of elements as heretofore set forth in the specification and shown in the drawings; it being understood that changes may be made in the embodiments disclosed without departing from the spirit and scope of the invention as defined in the following claims.

The embodiments of the invention in which an exclusive property or privilege is claimed are defined as follows:

1. A device for testing mine roof stability, comprising:
   means for exciting the mine roof to vibration at the natural occurring frequencies;
   transducer means sensing mine roof vibration to generate characteristic electrical signal output;
   gate means receiving input of said generated electrical signal output and providing a gate output signal for a predetermined duration;
   timing means responsive to said characteristic electrical signal output to turn on said gate means after a first predetermined duration;
   second timing means to turn off said gate means after a second predetermined duration;
   means for amplifying said gate output signal and providing an amplified output;
   filter means receiving said amplified output at a plurality of parallel inputs each to a respective one of plural frequency band filtering channels successively allotted within a predetermined total frequency range, each channel providing a band pass signal output;
   plural amplifier and indicator means each connected to a respective one of said channel signal outputs with each responsive to display indication when signals are detected within the respective designated frequency band.

2. A device as set forth in claim 1 wherein said plural amplifier and indicator means each comprise:
   amplifier means receiving the respective channel signal output to produce a frequency band output; and
   indicator means energized by the frequency band output.

3. A device as set forth in claim 2 wherein said indicator means comprises:
   a light-emitting diode.

4. A device as set forth in claim 1 which is further characterized to include:
   limiter means receiving the amplified output signal to produce only selected amplitude signals for input to said filter means parallel inputs.

5. A system for surveillance of mine roof stability, comprising:
   plural exciter means disposed at selected mine locations for exciting the mine roof to vibrations at the naturally occurring frequencies;
   plural acoustic detection means disposed adjacent respective ones of the plural exciter means;
   control means disposed at a selected location and effective to energize selected exciter means and to receive output from selected detection means;
   means for amplifying received outputs from selected detection means to provide a detection output;
   gate means receiving input of said detection output;
   timing means responsive to said detection output to turn on said gate means after a first predetermined duration;
   second timing means turning off said gate means after a second predetermined duration;
   filter means receiving said gate output at each of a plurality of inputs to provide plural filtered outputs of plural different frequency bands successively allotted within a predetermined frequency range; and
   plural amplifier and indicator means each connected to receive one of said filtered outputs and each responsive to display indication when sufficient signal is detected within the respective designated frequency band.

6. A system as set forth in claim 5 wherein said means for amplifying further includes:
   limiter means receiving signal output from said means for amplifying and providing detection output only for selected amplitude frequency response.

7. A system as set forth in claim 5 wherein each of said plural acoustic detection means comprises:
   an accelerometer disposed in contact to sense mine roof vibration.

8. A system as set forth in claim 5 wherein:
   at least some of said plural acoustic detection means are disposed to sense roof bolt vibrations.

9. A system as set forth in claim 5 wherein:
   at least some of said plural acoustic detection means are disposed to sense the mine roof formation.

* * * * *